United States Patent
Bigolin

(10) Patent No.: US 10,264,844 B2
(45) Date of Patent: Apr. 23, 2019

(54) SPORTS SHOE

(71) Applicant: Selle Royal S.p.A., Pozzoleone (Vicenza) (IT)

(72) Inventor: Barbara Bigolin, Asolo (IT)

(73) Assignee: SELLE ROYAL S.P.A., Pozzoleone (Vicenza), Italy (*) Notice: Subject to any disclaimer, the term of this patent is extended or adjusted under 35 U.S.C. 154(b) by 0 days.

(21) Appl. No.: 15/107,219

(22) PCT Filed: Dec. 23, 2014

(86) PCT No.: PCT/IB2014/067256
§ 371 (c)(1),
(2) Date: Jun. 22, 2016

(87) PCT Pub. No.: WO2015/097656
PCT Pub. Date: Jul. 2, 2015

(65) Prior Publication Data
US 2016/0331066 A1    Nov. 17, 2016

(30) Foreign Application Priority Data

Dec. 23, 2013   (IT) ............................. VR2013A0294

(51) Int. Cl.
*A43B 23/07*    (2006.01)
*A43B 5/04*    (2006.01)
(Continued)

(52) U.S. Cl.
CPC .......... *A43B 5/0405* (2013.01); *A43B 3/0005* (2013.01); *A43B 5/00* (2013.01);
(Continued)

(58) Field of Classification Search
CPC ................................. A43B 19/00; A43B 23/07
(Continued)

(56) References Cited

U.S. PATENT DOCUMENTS 1,902,780 A * 3/1933 Holden .................... D04B 1/26
36/55
3,729,779 A    5/1973 Porth
(Continued)

FOREIGN PATENT DOCUMENTS

CH         698108      5/2009
DE        29613358     8/1996
(Continued)

OTHER PUBLICATIONS

Office Action for U.S. Appl. No. 15/107,265 dated Feb. 23, 2018 (11 pages).

*Primary Examiner* — Marie D Bays
(74) *Attorney, Agent, or Firm* — Tutunjian & Bitetto, P.C.

(57) ABSTRACT

A sports shoe, including a sole and an upper that rises up from said sole, wherein the upper includes an inner part or core, in which the sports shoe and/or the inner part or core has an inner housing volume (RZ) for a foot of a user defined, during use, by an inner surface of the upper and by an inner surface of the sole and/or by the inner volume of the inner part or core, positioned inside the upper, including an upper-shaped portion and a ground resting portion, the latter adapted to come into contact with the ground or with the inner surface of the sole.

27 Claims, 5 Drawing Sheets

(51) Int. Cl.

| | | |
|---|---|---|
| A43B 19/00 | (2006.01) | |
| A43B 3/00 | (2006.01) | |
| A43B 5/14 | (2006.01) | |
| A43B 13/22 | (2006.01) | |
| A43B 5/00 | (2006.01) | |
| A61B 5/021 | (2006.01) | |
| A61B 5/08 | (2006.01) | |
| A61B 5/22 | (2006.01) | |
| A61B 5/00 | (2006.01) | |

(52) U.S. Cl.
CPC .............. *A43B 5/14* (2013.01); *A43B 13/223* (2013.01); *A43B 19/00* (2013.01); *A43B 23/07* (2013.01); *A61B 5/021* (2013.01); *A61B 5/0816* (2013.01); *A61B 5/221* (2013.01); *A61B 5/224* (2013.01); *A61B 5/4866* (2013.01); *A61B 5/6807* (2013.01); *A61B 2562/0252* (2013.01); *A61B 2562/0261* (2013.01)

(58) Field of Classification Search
USPC ........................................................ 36/10, 55
See application file for complete search history.

(56) References Cited

U.S. PATENT DOCUMENTS

| | | | |
|---|---|---|---|
| 4,326,320 A | 4/1982 | Riedel | |
| 4,550,446 A * | 11/1985 | Herman | A41B 11/00 2/239 |
| 4,937,952 A | 7/1990 | Olivieri | |
| 5,353,524 A * | 10/1994 | Brier | A41B 11/02 2/239 |
| 5,499,459 A * | 3/1996 | Tomaro | A43B 1/0045 36/10 |
| 5,595,005 A * | 1/1997 | Throneburg | A41B 11/00 36/10 |
| 5,617,585 A * | 4/1997 | Fons | A41B 11/007 2/239 |
| 5,802,740 A * | 9/1998 | Merk, Sr. | A43B 7/125 36/10 |
| 5,855,079 A * | 1/1999 | Herbert | A43B 3/0047 36/10 |
| 5,964,047 A * | 10/1999 | Covatch | A43B 7/34 36/10 |
| 7,140,129 B2 * | 11/2006 | Newson | A43B 5/18 36/100 |
| 7,392,990 B2 | 7/2008 | Bussiere | |
| 7,836,612 B2 * | 11/2010 | Agnew | A43B 5/0405 36/10 |
| 7,900,379 B2 * | 3/2011 | Lafortune | A43B 7/142 36/100 |
| 8,032,993 B2 | 10/2011 | Musal | |
| 8,065,818 B2 * | 11/2011 | Greene | A43B 9/00 12/142 E |
| 8,763,209 B2 | 7/2014 | Kavarsky et al. | |
| 9,498,023 B2 * | 11/2016 | Craig | A43B 1/04 |
| 2001/0018805 A1 * | 9/2001 | Basso | A43B 1/0081 36/10 |
| 2004/0025374 A1 * | 2/2004 | Basso | A43B 1/0081 36/10 |
| 2004/0128863 A1 * | 7/2004 | Hong | A43B 3/24 36/100 |
| 2004/0244221 A1 | 12/2004 | Hall et al. | |
| 2005/0066544 A1 * | 3/2005 | Beak | A41B 11/008 36/43 |
| 2007/0011912 A1 * | 1/2007 | Clark | A43B 1/14 36/50.1 |
| 2007/0094892 A1 * | 5/2007 | Craig | A41B 11/02 36/10 |
| 2008/0287832 A1 | 11/2008 | Collins et al. | |
| 2009/0000152 A1 | 1/2009 | Agnew et al. | |
| 2009/0018428 A1 * | 1/2009 | Dias | A41D 13/1281 600/388 |
| 2009/0100713 A1 * | 4/2009 | Adami | A43B 3/0047 36/100 |
| 2009/0199435 A1 | 8/2009 | Robinson, Jr. et al. | |
| 2010/0086747 A1 * | 4/2010 | Plant | A41D 31/005 428/188 |
| 2010/0236100 A1 * | 9/2010 | Ho | A43B 1/0081 36/100 |
| 2011/0258876 A1 | 10/2011 | Baker et al. | |
| 2012/0004587 A1 | 1/2012 | Nickel et al. | |
| 2012/0011744 A1 * | 1/2012 | Bell | A43B 1/0072 36/91 |
| 2012/0030965 A1 * | 2/2012 | Greene | A43B 9/00 36/10 |
| 2012/0144700 A1 | 6/2012 | Zhao et al. | |
| 2012/0240428 A1 | 9/2012 | Knoll | |
| 2013/0014359 A1 | 1/2013 | Chen | |
| 2014/0090274 A1 * | 4/2014 | Arquilla | A43B 1/0045 36/83 |
| 2014/0123449 A1 | 5/2014 | Soderberg et al. | |
| 2014/0137434 A1 * | 5/2014 | Craig | A43B 1/04 36/54 |
| 2015/0245688 A1 * | 9/2015 | Young | A43B 19/00 36/10 |
| 2015/0376821 A1 * | 12/2015 | McMaster | D04B 1/102 66/202 |
| 2016/0120733 A1 * | 5/2016 | Ishikawa | A43B 3/0005 601/151 |
| 2016/0367191 A1 * | 12/2016 | Esposito | A61B 5/1038 |

FOREIGN PATENT DOCUMENTS

| | | |
|---|---|---|
| DE | 29701491 | 5/1998 |
| DE | 202004007174 | 10/2005 |
| EP | 1421868 | 5/2004 |
| WO | WO2010096691 | 8/2010 |

\* cited by examiner

TABLE 1

| | EXTRA SOFT | SOFT | MEDIUM SOFT | MEDIUM HARD | HARD | EXTRA HARD |
|---|---|---|---|---|---|---|
| SHORE OO | 20  30  35  40  50 | 55  60 | 70 | 80 | 90  95  98 | |
| SHORE A | | 10  20  30 | 40 | 50  60 | 70  80 | 90  95  100 |
| SHORE D | | | | | 22  25  35 | 45  55  65  75 |

FIG. 9

SPORTS SHOE

TECHNICAL FIELD OF THE INVENTION

The present invention relates to a sports shoe, for example a running shoe or shoe for cycling or for sports such as skiing, snowboarding or the like, and, in particular, the inner portion or core of such sports shoe.

STATE OF THE PRIOR ART

Sports shoes generally comprise an upper, made of more or less strong material, and a sole, possibly shaped so as to be adapted to the sport for which they are ideated. Sports shoes also comprise the inner part of the upper generally made of breathable material, in order to obtain a certain level of comfort for the user. Such inner part is usually integral or made of a single piece with the upper itself.

In addition, cycling shoes have a sole equipped, in its lower part, with a system of coupling to the pedal of the bicycle, which is used during pedalling but which is not easy and can be damaged when the user must use such shoes for walking.

Other shoe types, such as ski and snowboard boots, are very rigid and also have a sole provided with a specific shape for attaching to the ski or snowboard. Also in this case, for the user who wears such boots, walking is not comfortable and is not easy to carry out.

Such sports shoes, moreover, in order to ensure optimized performances, require that the foot of the user be very adherent to the upper in order to control the movement. In addition, the shoe per se requires being of limited weight and having good aerodynamic characteristics.

In addition, shoes are sought that increase the comfort for the user and facilitate user movements even in walking, and hence are comfortable and versatile even when the user is not specifically executing the athletic action.

There has thus been perceived the need to provide a sports shoe which, in addition to the normal requirements of limited weight and increased control of foot movements, also provides high user comfort, for the entire time in which the shoes are or must be worn, and thus not only during the execution of the sport for which they were conceived.

SUMMARY OF THE INVENTION

The technical task of the present invention is to improve the state of the prior art. In the scope of such technical task, one object of the present invention is to obtain a sports shoe that is comfortable for the user.

Another object of the present invention is to provide a shoe that gives good sports performance to the user, maintaining a limited weight and the control of foot movements.

A further object of the present invention is to provide a shoe that can be comfortably used even when the user must walk, and hence not only during the execution of the athletic action.

This task and these objects are attained by a sports shoe according to the principles of the present specification.

The present specification refers to preferred and advantageous embodiments of the invention.

BRIEF DESCRIPTION OF THE DRAWINGS

Other characteristics and advantages of the invention will be more evident from the description of embodiments of a shoe, illustrated by way of example in the set of drawings, in which:

FIG. 9 depicts an exemplary Shore hardness scale shown as Table 1.

In the set of drawings, equivalent components or parts are marked by the same reference numbers.

DETAILED DESCRIPTION OF THE INVENTION

With reference to the enclosed figures, reference number 1 indicates overall a sports shoe according to the present invention.

The following description and enclosed drawings, while referring to a sports shoe for cycling, are intended for any type of sports shoe, without at all limiting the specifically illustrated example.

The shoe 1 comprises a sole 2.

The shoe 1 also comprises an upper 3. The upper 3 rises up from the sole 2.

Figure 1:
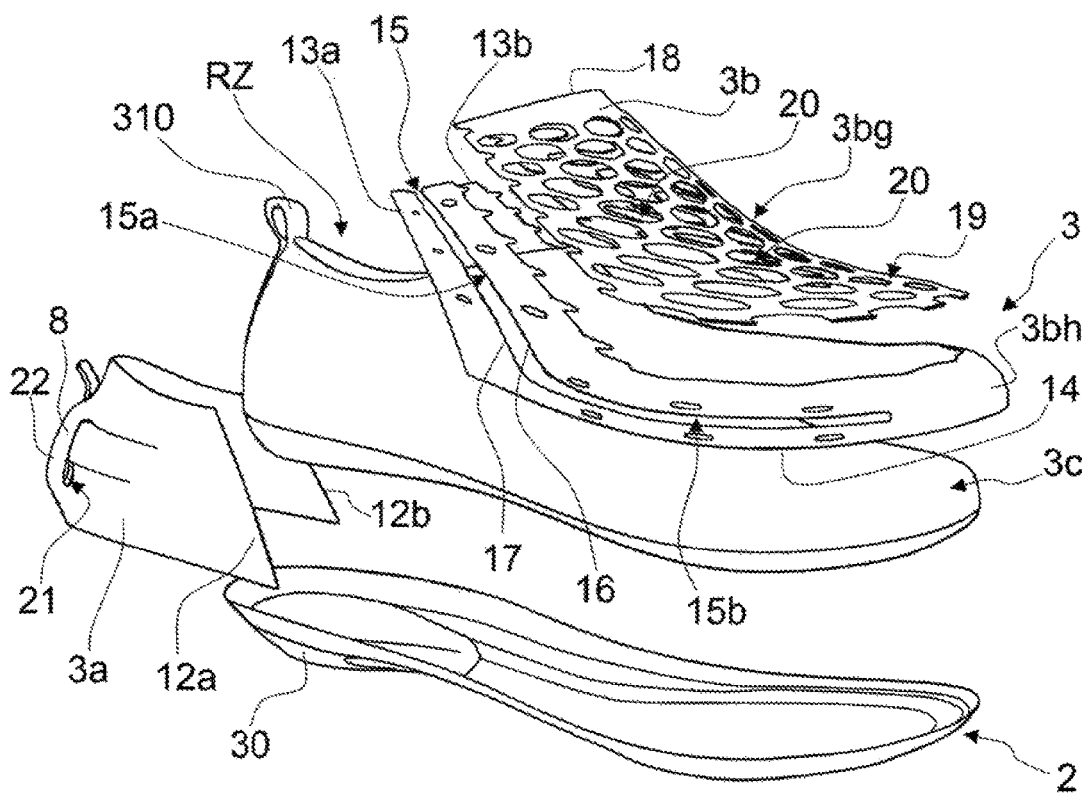
FIG. 1 is an exploded perspective view of the shoe according to the present invention.
Figure 3:
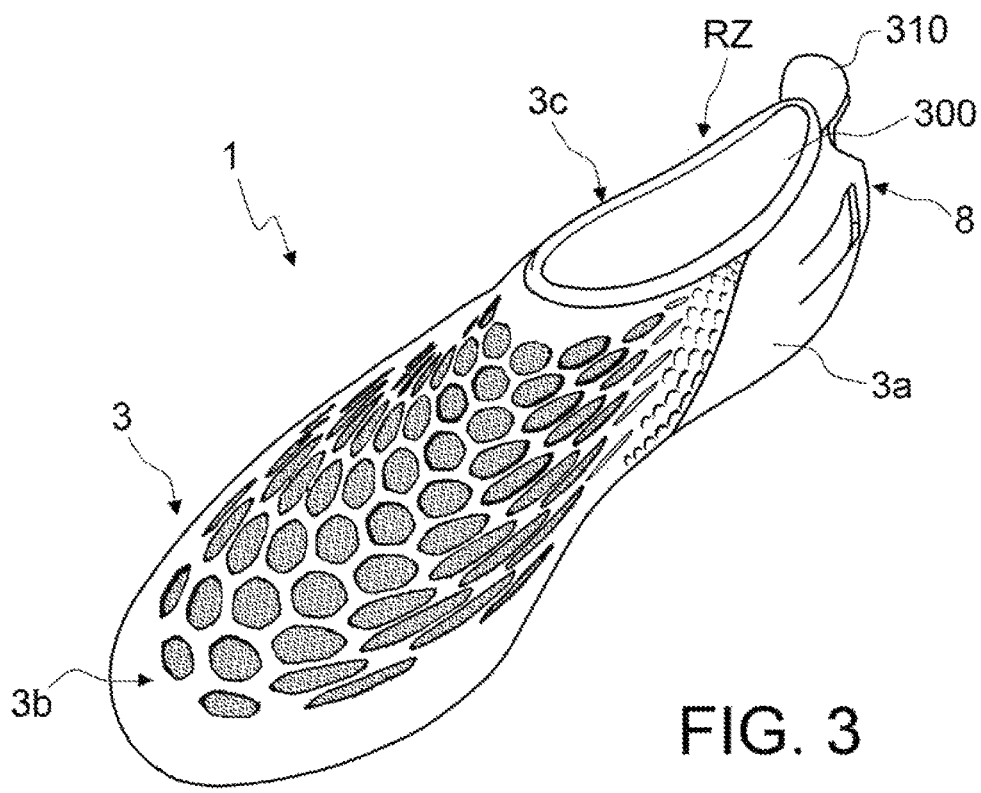
FIG. 3 is a perspective view of a version of the shoe according to the present invention.
Figure 4:
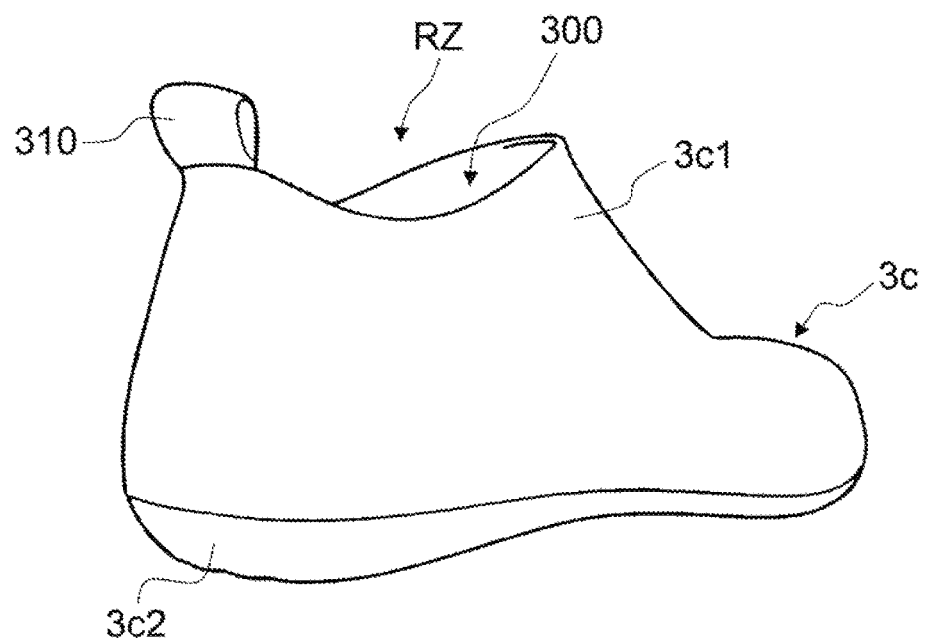
FIG. 4 is a rear view of the inner part or core of the shoe according to the present invention.
Figure 5:
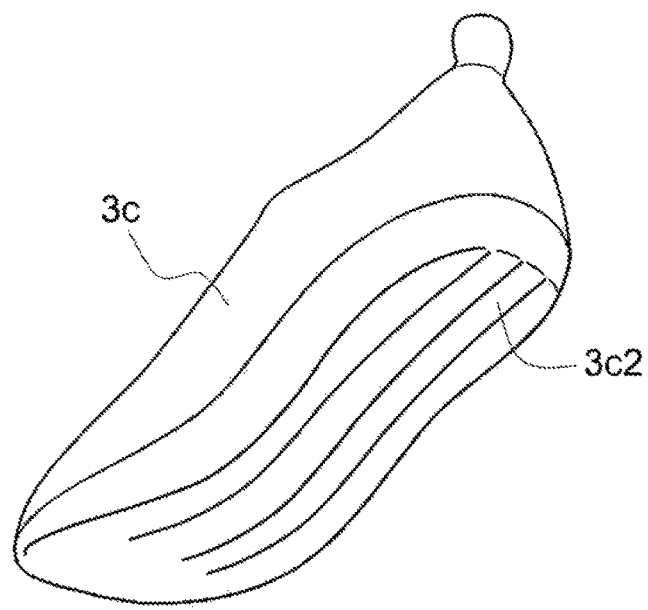
FIG. 5 is a bottom rear view of the inner part or core pursuant to FIG. 4.
Figure 6:
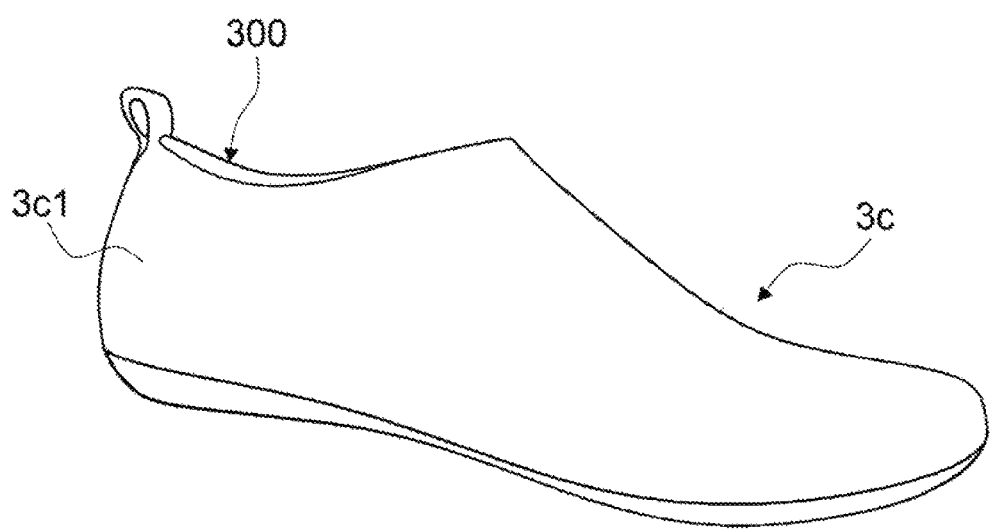
FIG. 6 is a side view of the inner part or core pursuant to FIGS. 4 and 5.

In one version of the invention, for example illustrated in FIGS. 1 and 3, the upper 3 can comprise two or more portions 3a, 3b at least partially mutually displaceable (i.e. with respect to each other).

With regard to the mutually displaceable portions, these can be displaced with respect to each other and can both be movable, or one fixed and the other movable with respect to the first.

In such version, in particular, the upper 3 comprises a fixed portion 3a and a movable portion 3b at least partially displaceable with respect to the fixed portion 3a, thus to adjust the housing size or volume RZ for a foot of a user inside the shoe 1.

In addition, the shoe 1 or the upper 3 comprises an inner part or core 3c. The inner part or core 3c is an inner covering or liner of the upper 3.

The housing volume RZ for a foot of a user is inside the shoe 1 and/or the inner part or core 3c.

The inner housing volume RZ for the foot of the user is defined, during use, by an inner surface of the upper 3 and by an inner surface of the sole 2.

The inner part or core 3c defines the housing volume RZ for the foot of the user. Around the inner part or core 3c, the upper 3 is positioned, or in a specific version, the at least partially mutually displaceable portions 3a, 3b are mounted and positioned.

The inner part or core 3c is made of an elasticated fabric and/or of woven material. It acts as inner sock of the shoe 1 or as inner and breathable part of the upper 3.

The inner part or core 3c can substantially act as a sock for the user, who can put on, for the reasons described in detail hereinbelow, the sports shoe 1 without previously putting on a traditional sock.

The inner part or core 3c can be personalised for the user, since a "winter" version can be provided, for example made of a material capable of protecting the foot from cold; a "summer" version can be provided, e.g. made of a material capable of protecting the foot from heat or capable of ensuring greater breathability, or made with lower material thicknesses; or any "intermediate" version can be provided, e.g. for the spring or fall.

The inner part or core 3c can also have specific windbreaker materials, in order to increase the comfort and the performances of the user.

The material with which the inner part or core 3c of the shoe 1 is made, in one version of the invention, is impermeable.

In one version of the invention, the inner part or core 3c of the sports shoe 1 can be provided with different characteristics or with optional additions, depending on the needs of the user.

The inner part or core 3c is removable from the shoe 1. In particular, said upper 3 and said inner part or core 3c, in one version of the invention, have mutual constraints of removable type.

In one further version of the invention, the inner part or core 3c does not have constraints with the upper 3. In this case, the inner part or core 3c is fixed to the foot through the tightening of the upper itself of the shoe on the user's foot.

Such characteristic, as will be better explained hereinbelow, confers to the user great versatility in the use of the shoe 1 itself.

In such a manner, the user is for example able to extract the inner part or core 3c from the shoe 1. Since the cycling shoe 1 has a sole provided with the system of coupling to the pedal of the bicycle, the user, having extracted the inner part or core 3c, can then easily walk, not burdened by a rigid upper and/or by a sole provided with attachment systems, and without the risk of damaging the same.

In addition, due to the fact that it is removable, the inner part or core 3c can be easily washed and reused.

Given that it is removable, the inner part or core 3c can be replaced, depending on the needs or in case of damage and wear.

According to such advantage, the inner part or core 3c itself acts as a shoe and, according to such specific use, in such inner part or core 3c, an upper-shaped portion 3c1 or portion which acts as upper (when the inner part or core 3c is drawn from the shoe 1) and a ground resting portion 3c2 or portion which acts as sole portion (when the inner part or core 3c is drawn from the shoe 1) can be distinguished.

The upper-shaped portion 3c1 erects from the ground resting portion 3c2.

The upper-shaped portion 3c1 delimits a hole 300 for insertion of the user's foot, and is constituted by an annular and/or tubular component.

In particular, considering that the hole 300 lies on a plane substantially parallel to the ground and its peripheral edge having a transversal section substantially lying on this plane, the upper-shaped portion 3c1 or its annular and/or tubular component has a side wall having transversal section gradually greater, starting from the hole 300 till the ground resting portion 3c2.

In a version of the invention, the upper-shaped portion 3c1 is made in a single piece.

In particular, the upper-shaped portion 3c1 is adapted to come into contact with the upper 3 of the shoe 1 and with the foot of the user; the ground resting portion 3c2 is adapted to come into contact with the sole 2 of the shoe 1 and with the foot of the user, in particular with the part of the sole 2 directed towards the foot of the user. Therefore, the ground resting portion 3c2 of the inner part or core 3c can come into contact with the ground, when extracted from the shoe 1, or with the inner surface of the sole 2, when inserted into the upper 3.

The inner part or core 3c is made in a manner so as to be perfectly adherent to the foot of the user; in such a manner, the user itself will not be disturbed, during the execution of the athletic action, by the presence of the inner part or core 3c-neither from the comfort standpoint, nor from the sports performance standpoint.

In addition, in this manner, the inner part or core 3c is adapted to any size of the foot of the user, eliminating particular pressure points on the foot itself.

For example, in one version of the invention, the ground resting portion 3c2 can have a series of grooves or protrusions, e.g. conical or cylindrical, adapted to be fit in a complementary manner with respective channels or recesses, e.g. conical or cylindrical, present in the inner part of the sole 2 of the shoe 1. In such a manner, the inner part or core 3c is positioned in a stable manner inside the shoe 1, without there being movements of the inner part or core 3c with respect to the inner part of the sole 2 of the shoe itself. This advantage improves the performances of the user.

The inner part or core 3c is made, as stated above, of an elasticated fabric and/or of a woven material. Such mesh occurs through circular machines and therefore the woven material is substantially a woven tubular element that does not have stitching. In a version of the invention, the inner part or core 3c is made in a single piece and can be worn on the foot of the user through the hole 300, which will be better defined below, thanks to the elasticity of the material with which the inner part or core 3c is made.

The material with which the inner part or core 3c is made may have, in a version of the invention, a Shore 00 hardness comprised in the range of about 50 to 70. It is therefore classified as soft.

Indeed, the materials are usually classified as follows (see table 1 shown in FIG. 9).

Extra soft: Shore 00 from 20 to 50 (e.g. chewing gum and racquetball balls),

Soft: Shore 00 from 50 to 70 (e.g. rubber band),

Medium soft: Shore 00 from 70 to 80 (e.g. pencil eraser),

Medium hard: Shore 00 from 80 to 95 (e.g. tyre),

Hard: Shore 00 higher than 95 or Shore D from 22 to 35 (e.g. the heel of a shoe), Extra hard: Shore D from 35 to over 75 (e.g. wheels of shopping carts or rigid material caps).

A possible material usable for the inner part or core 3c, or at least for its upper-shaped portion 3c1, is, as stated, an elasticated material and/or a woven fabric such as: fabric with high breathability laminated with a layer of foam, like for example that commercialised with the name Aeriaprene, or a synthetic rubber based on polychloroprene (polymer form of chloroprene), like for example that commercialised with the name Neoprene, possibly coupled with a fabric for example made of a synthetic polyurethane fibre, for example lycra or elastam, or microfiber, or a synthetic fabric with high impermeability and breathability capabilities, consisting of microporous polytetrafluoroethylene, for example that commercialised with the name Goretex or other breathable fabrics.

Such material confers the following advantages to the inner part or core 3c: limited weight, anti-odor, breathability, easy washability.

Another material usable for the inner part or core 3c, or at least for its upper-shaped portion 3c1, can be a three-dimensional mesh comprising at least one thread of thermosetting polyester. Also in this case, the properties of limited weight and high breathability are ensured.

In a further version of the invention, the material with which the inner part or core 3c is made is a composite yarn material comprising fibres, such as carbon fibres, able to assume the desired shape, possibly without being thermoformed. In one version of the invention, the inner part or core 3c comprises a yarn capable of conferring to the inner part or core 3c a "device" character, capable of detecting the physiological or vital parameters of the body of the user. Such yarn, in fact, is adapted to read and detect such physiological or vital parameters, such as blood pressure, calorie consumption, number of respirations or heart beats for example per minute, the oxygenation, comfort and positioning of the foot of the user, possible muscular stress, potassium transport, the power exerted by the foot for example on the pedal of the bicycle, etcetera.

The yarn in question can, for example have systems for detecting the aforesaid parameters or transistors or load cells or a strain gauge, etcetera, in order to detect the requested values; the collected data can be recorded or transmitted according to normal modes. The yarn in question can be inserted in the elasticated fabric and/or in the woven material that constitutes at least part of the inner part or core 3c or it can substitute such inner part or core 3c.

In one version of the invention, the inner part or core 3c can have a constant thickness for its entire extension, during use longitudinal or front-back and/or transversal or side-side, with respect to said shoe.

In an alternative version, the thicknesses of the various zones that constitute the inner part or core 3c can vary depending on the requirements.

For example, it is possible to have greater thicknesses at the ground resting areas of the user's foot, and/or at the back of the foot, in a manner so as to confer a good sensation of resting and support to the user, as well as a good adhesion of the inner part or core 3c itself to the foot, during the execution of the sports action, e.g. pedalling, in a manner such that the energy developed by the movement is nearly completely transferred for example to the pedal or to the ski.

For example, in one version of the invention, the thickness of the ground resting portion 3c2 is about 5 mm in the rear portion of the heel 8.

Due to the possibility to vary the density of the meshes that constitute the elasticated fabric and/or the woven material of the inner portion or core 3c, it is possible to create a differentiated thickness in the same portions, without having to add different material layers, such as a foam, in order to vary the thickness of a specific zone.

Nevertheless, the overall thickness of the inner part or core 3c is such to not interfere with the athletic performances and the transfer of energy from the user to the sole 2 during the sports action.

In addition, in the inner part or core 3c, areas with differentiated compression can be provided, for example in the part of the plantar arch or instep of the foot, so as to ensure an improved fitting of the inner part or core 3c.

Figure 7:
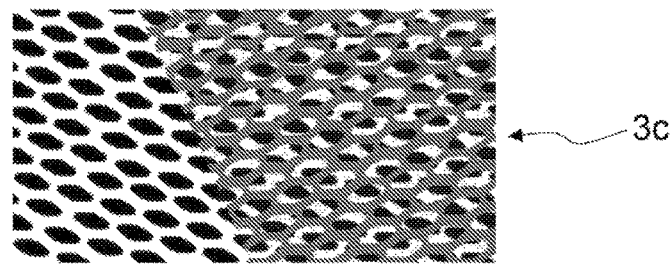
FIG. 7 is an enlarged detail of the inner part or core of a version of the shoe according to the present invention.

Illustrated in FIG. 7 is an enlarged detail of the elasticated fabric and/or of the woven material that constitutes the inner part or core 3c. Such material, as is visible, comprises a series of meshes connected together, which can simultaneously allow the breathability of the foot, the softness of the fabric, and if necessary also the impermeability thereof.

For example, such meshes can constitute a net provided with through or partially-through openings.

In addition, as stated, such specific material is knitted in a manner so as to be without stitching or having only one stitching in the rear part of the heel 8 of the inner part or core 3c or of the shoe 1, i.e. at the heel area of the user's foot.

Such single stitching, if present, can alternatively be positioned at a point of smaller pressure for the foot, in a manner so as not to make the user who wears such inner portion or core 3c and/or such sports shoe 1 uncomfortable.

The material with which the ground resting portion 3c2 of the inner part or core 3c is obtained may have a Shore 00 hardness comprised between approximately 70 and 80. It is therefore classified as medium soft.

The ground resting portion 3c2 can, in one version of the invention, be made of a polymeric material having the indicated hardness, such as rubber or silicone or polyurethane, or thermoplastic rubbers or vulcanised rubber.

In the version in which the ground resting portion 3c2 is made of a polymeric material, such material can be applied to the fabric or woven material of the inner part or core 3c by means of moulding, gluing, stitching, welding or any other method suitable for the purpose. In addition, the polymeric material of the ground resting portion 3c2 can have a surface pattern for resting on the ground similar to that of a tread, or equipped with non-slip grooves.

In one version of the invention, the ground resting portion 3c2 of the inner part or core 3c is composed of a layer of the aforesaid polymeric material, connected at its peripheral part to the upper-shaped portion 3c1. In other words, in the ground resting portion 3c2 there is no fabric or woven material that constitutes the inner part or core 3c. In such case, the fabric or woven material is of conventional, non-circular type.

Alternatively, the polymeric material layer can cover the fabric or woven material that constitutes the upper-shaped portion 3c1, possibly being impregnated thereon.

The ground resting portion 3c2 comprising polymeric material is extended over the entire length of the foot of the user and possibly partially rises on the lateral edges thereof; in other words, it has an extension at least partially corresponding with the length and/or width of the foot of the user or equal to the length and/or width of the foot of the user for its entire extension, during use longitudinal or front-back and/or transversal or side-side, and/or comprises lateral portions at least partially rising on the lateral edges of the user's foot.

The ground resting portion 3c2 of the inner part or core 3c is also cushioning.

In one version of the invention, illustrated in the figures, the inner part or core 3c has a hole 300 for inserting the foot of the user and it defines the space occupied by the foot itself RZ.

At the hole 300 for the entrance of the foot, in the rear part of the heel 8, the inner part or core 3c has a tongue 310, in a manner such that the user can grasp such tongue 310 and thus facilitate the insertion and/or extraction of the foot in the inner part or core 3c or upon exiting from the same.

Figure 2:
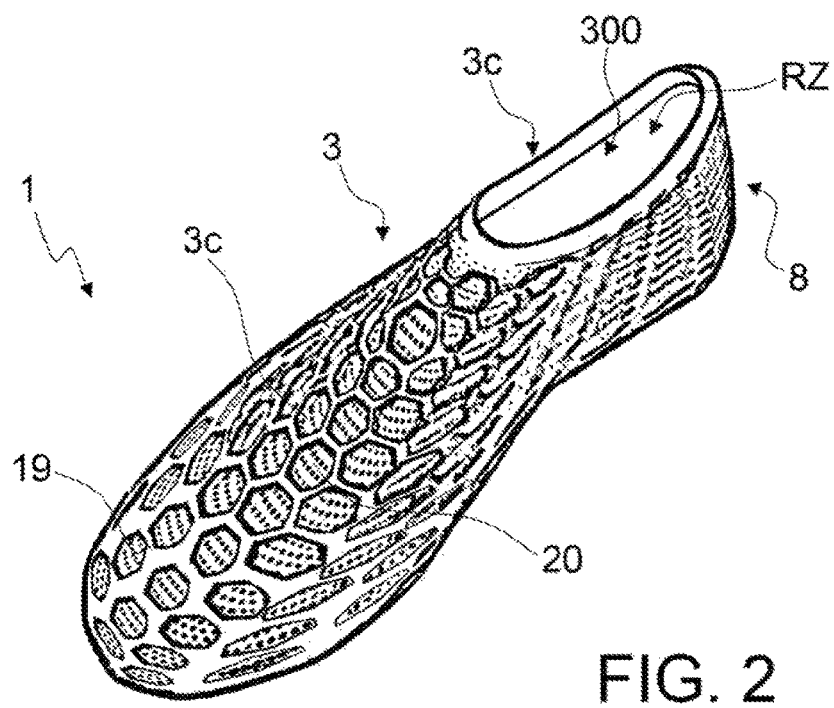
FIG. 2 is a perspective view of the shoe according to the present invention.

In an alternative version of the invention, illustrated in FIG. 2, the tongue 310 is not present.

In one embodiment of the invention, as mentioned above, the mutually displaceable portions 3a, 3b of the upper 3 are constituted by mask components mounted around, and to cover or enclose, the inner part or core 3c; in such case, by mutually moving the mutually displaceable portions 3a, 3b it is possible to modify the shape or configuration of the inner part or core 3c, thus varying the housing volume RZ. The displaceable portions 3a, 3b can be made of a material more rigid than the inner part or core 3*c*, for example of a plastic or composite material.

The inner part or core 3*c* can be constrained to the upper 3 of the sports shoe 1 in a removable manner, for example through constraining means of removable type. In one version of the invention, the inner part or core 3*c* is only inserted in the upper 3, without being constrained to the upper itself.

It has thus been seen that the inner part or core 3*c* is actually able to produce the abovementioned advantages, given that it is light, versatile and comfortable.

Figure 8:
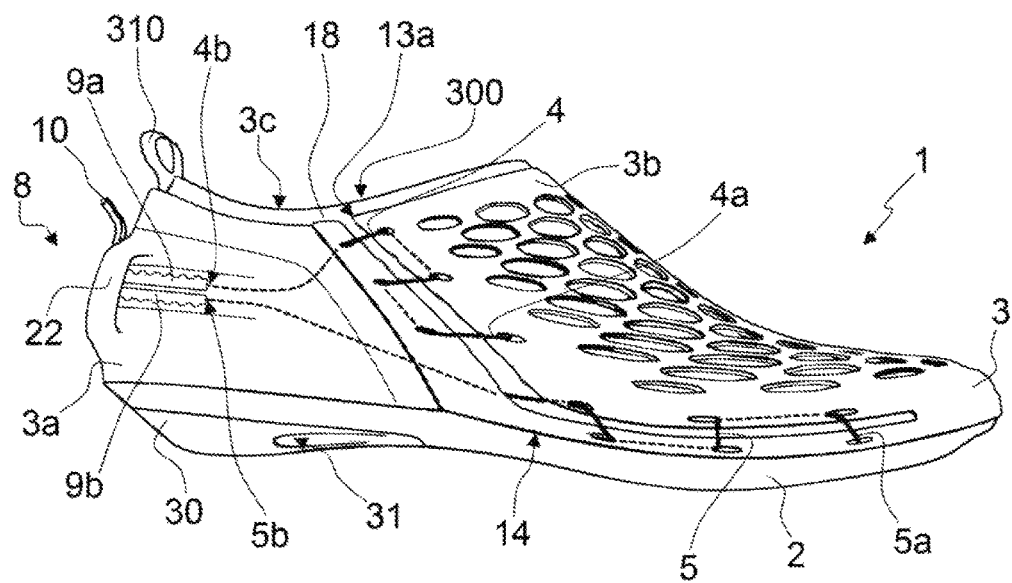
FIG. 8 is a side view of the shoe according to the present invention.

The shoe 1 comprises tightening-release means 4, 5 for the mutually displaceable portions 3*a*, 3*b* of the upper 3. In a non-limiting example of the present invention, as visible in FIG. 8, the tightening-release means 4, 5 are applied to a cycling shoe.

According to one embodiment of the invention, the tightening-release means 4,5 can for example comprise one or a plurality of cable elements 4, 5, two according to the illustrated example. The cable elements, in one version of the invention, are made of steel.

The cable elements 4,5 comprise respective first ends 4*a*, 5*a* fixed to one of the mutually displaceable portions 3*a*, 3*b*, preferably to the movable portion 3*b*.

The cable elements 4,5 also comprise respective second ends 4*b*, 5*b*, engageably adjustable with the other of the mutually displaceable portions 3*a*,3*b*, preferably with the fixed portion 3*a*.

According to another aspect of the present invention, the shoe 1 comprises means for controlling the tightening-release means 4, 5.

The control means can be operatable or arranged at the back of the shoe 1, preferably at the heel 8 of the shoe 1, i.e. that part intended to enclose the heel or in any case the rear part of the foot of a user.

In one embodiment, the control means include at least one component for longitudinal approach and/or removal of the mutually displaceable portions 3*a*, 3*b*, i.e. which operates along the front-back longitudinal axis of the shoe 1.

In addition, the control means can comprise a component for lifting and/or lowering one of the mutually displaceable portions 3*a*, 3*b* with respect to the other.

The component for longitudinal approach-removal is intended to control the tightening-release means 4: i.e. to tighten, in the front-back direction, the mutually displaceable portions 3*a*, 3*b*, so as to engage the inner part or core 3*c* from the front towards the back, or vice versa.

Preferably, the approach-removal component is intended to move at least part of the movable portion 3*b* towards the back and towards the fixed portion 3*a*, so as to tighten the inner part or core 3*c*; or the approach-removal component is intended to move at least part of the movable portion 3*b* towards the front (or away from the fixed portion 3*a*), so as to allow a widening of the inner part or core 3*c*.

The lifting component is instead intended to control the tightening-release means 5 so as to vertically and mutually tighten the two portions or parts of the mutually displaceable portions 3*a*, 3*b* and to tighten the inner part or core 3*c* by means of the portions 3*a*, 3*b* from bottom to top or vice versa.

Preferably, the lifting component is intended to move at least part of the movable portion 3*b* downward and towards the fixed portion 3*a*, so as to tighten the inner part or core 3*c*, or upward or away from the fixed portion 3*a*, so as to release the inner part or core 3*c*.

Still more preferably, the control means comprise at least one pinion component mounted on one of the mutually displaceable portions 3*a*, 3*b*, if desired on a fixed portion 3*a*, as well as a rack element 9*a*, 9*b* constrained on one side to a respective cable element 4, 5 fixed to the other of the mutually displaceable portions 3*b*, and on the other side engageable by means of one or a respective pinion component.

A first end of a rack element 9*a*, 9*b* can be fixed to a respective cable element 4, 5 for example via gluing, welding or by means of insertion and locking of a cable element 4, 5 in a slot formed in such first end.

The other or second end of the rack element 9*a*, 9*b* can be free, while an intermediate portion of the rack element is slidably mounted in meshing engagement with a respective pinion component.

The pinion component can be rotatably mounted around a substantially horizontal axis or in the front-back direction, e.g. transverse to the upper and from the outside towards the inside thereof, while the at least one rack element 9*a*, 9*b* can have preferably substantially horizontal position and be extended in a direction around the housing volume RZ.

A pinion component can be rotatably mounted in the heel 8, while a respective rack 9*a*, 9*b* is slidably guided in meshing engagement with a respective pinion element.

For such purpose, the fixed portion 3*a* can have, overall or in part, a closed shell-like body delimiting a suitably-shaped zone for the sliding and guiding of the at least one rack element 9*a*, 9*b*, in which also the at least one pinion element projects.

If desired, the shell-like body of the fixed portion 3*a* can comprise projecting parts or parts in relief delimiting the sliding and guiding zone of the at least one rack element 9*a*, 9*b*.

Advantageously, the at least one cable element 4,5 engages the movable portion 3*b* at a plurality of zones, such that by controlling the operation of the control means, an overall and non-localised tightening or release is determined of the two mutually displaceable portions 3*a*, 3*b*.

For such purpose, a cable element 4 can be constrained to the movable portion 3*b* in an intermediate or lower zone thereof and returned one or more times (three according to the illustrated embodiment) between movable portion 3*b* and fixed portion 3*a* or between separated sections of one of such portions 3*b*.

This can for example be obtained by means of the passage or subsequent return of the cable element 4 in eyelets formed in such portions 3*a*, 3*b* or in the sections of a portion 3*b*.

The eyelets are arranged at different levels of the upper and of one or both portions 3*a*, 3*b*, until the cable element 4 reaches or projects at the top of a rear edge 13*a* of the movable portion 3*b*, hence a front edge 12*a* of the fixed portion 3*a* and from here is conveyed to the control means, hence, if provided, to the respective rack element 9*a*. If desired, in the fixed portion 3*a* and/or in the movable portion 3*b*, insertion grooves can be provided for the guiding and sliding of the cable element 4.

The cable element 4 can constitute a component for longitudinal or front-back approach-removal of the control means.

A cable element 5 can also be constrained to the movable portion 3*b* in a front zone thereof and be returned one or more times (three according to the illustrated embodiment) between movable portion 3*b* and fixed portion 3*a* or between sections of one of such portions 3*b* by means of passage of the cable element 5 in respective eyelets arranged at zones with different longitudinal position of the upper, until a rear edge 13*a* of the movable portion 3*b* is reached and from here be conveyed towards a front edge 12a of the fixed portion 3a and then to the control means, hence if provided to the respective rack element 9b.

Also in such case, if desired in the fixed portion 3a and/or in the movable portion 3b, grooves can be provided for the insertion and sliding of the cable element 5. The cable element 5 can represent a component 7 for the mutual lifting-lowering of the mutually displaceable portions 3a, 3b.

According to one embodiment, the first cable element 4 is upper during use and is extended from the respective rack element 9a to a front edge 12a, if desired at the top of such edge, of the fixed portion 3a and from here it is extended beyond the fixed portion 3a until it engages the movable portion 3, if desired at the top thereof. One or more pinion components can also have an outer head or head projecting outside the sole 2; also able to extend from the outer head is a toothed wheel or the like or a stem on which a toothed wheel is mounted.

Advantageously, the control means also comprise a lever 10 for controlling the rotation of the pinion component, which can be elastically loaded.

Preferably, the control lever 10 is elastically loaded, but it is disengaged from the respective pinion component 6 after having controlled the rotation thereof, such that—after a respective angular movement or actuation thereof with consequent rotation of the pinion component 6—it returns to rest position, for example substantially vertical position and free grip portion that is extended upward. The control lever 10 can, therefore, be a kind of "ratchet" or "ratchet key" with position return spring and allows a snap adjustment with fixed pitch of the pinion component 6. Due to such expedient, the user always knows the position of the lever 10 (e.g. substantially vertical) and is able to reach it and control it appropriately also during the execution of a sport, e.g. during pedalling.

Advantageously, the control lever 10 is substantially curved, e.g. helical, so as to provide an easy grip surface for the user, e.g. for a thumb thereof.

Alternatively, in the outer head of a pinion component, an engagement seat can be delimited for an actuation tool, e.g. a screwdriver or Allen spanner.

In addition, a pinion component can be displaceable between a rest position (in which the mutually displaceable portions 3a,3b are loosely constrained to each other so as to not reduce the housing size or volume RZ) and a work position (in which the mutually displaceable portions 3a,3b are constrained to each other as in FIG. 1, i.e. rigidly constrained in a manner so as to reduce—or adapt to the specific size of the foot of the user—the housing size or housing volume RZ); in such work position, the pinion component is rotated with respect to the rest position, and a release button is provided for the pinion intended to take such pinion back into rest position.

With regard to the mutually displaceable portions 3a, 3b, in a version of the invention illustrated in the figures, these can comprise a substantially front tongue part 3b as well as a lateral-rear part 3a, if desired U-shaped, e.g. with section increasing downward, which can be constrained to each other.

The tongue part 3b can have two rear edges 13a, 13b, respectively one on one side or inner side of the shoe and the other 13b on the other side or outer side of the shoe, fixed to the lateral-rear part or better yet to respective front edges 12a, 12b (one on one side and the other on the other side of the fixed portion 3a), as well as a lower edge 14 fixed to the sole 2. In the tongue part 3b, preferably on the outer side of the shoe, i.e. the side during use directed away and not towards the other shoe worn by the user, a groove 15 can then be formed so as to delimit two inner edges 16, 17 therein, while the tightening-release means 4, 5 for the mutually displaceable portions are intended to tighten-release the inner edges 16, 17 of the tongue part 3b, and consequently to tighten-release one section of the movable portion 3b with respect to the other section and thus with respect to the fixed part 3a.

The groove 15 can be extended from the free upper edge 18 of the tongue portion 3b up to the tip thereof. More particularly, the groove 15 can have a first section 15a that is extended from the upper edge 18 and with slightly oblique progression or with lower end in a more advanced position or proximal to the front with respect to the upper end, and then a second section 15b substantially horizontal or parallel to the sole 2.

In such case, the cable element 4 can be returned between inner edges 16, 17 of the movable portion 3b at the first section 15a, while the cable element 5 can be returned between inner edges 16, 17 of the movable portion 3b at the second section 15b.

Illustrated in exploded view in FIG. 1 is a shoe 1 according to the present invention, in which the single components can be observed.

In addition, in the version illustrated in FIG. 1, the movable portion 3b can be provided in two separate portions 3bg, 3bh. Such separate portions 3bg, 3bh can be fixed together by means of moulding, fitting, welding or other technique.

The portion 3bg is frontal and substantially covers the back of the foot of the user.

The portion 3bh is peripheral and comprises the groove 15. Such portion 3bh acts as a bumper for the shoe itself.

The portions 3bg, 3bh, when assembled, constitute the movable portion 3b.

The tongue part 3b or its portions 3bg, 3bh can for example be made of multiple layers or components, each made of a material with different hardness with respect to the others.

For example, the front part of the tongue 3b or the portion 3bg can be made of a soft material, having Shore 00 hardness from 50 to 70; the peripheral part of the tongue 3b or the portion 3bh can be made of a medium soft material, having Shore 00 hardness from 70 to 80.

The fixed portion 3a can for example be made of multiple layers or components, each made of a material with different hardness with respect to the others.

For example, the fixed portion 3a or its closed shell-like body can be made of a medium soft material, having Shore 00 hardness from 70 to 80; the suitably-shaped sliding and guiding zone of the rack element(s) 9a, 9b, in which also the pinion element/elements 6, 7 projects/project, or the projecting parts or parts in relief delimiting the sliding and guiding zone of the rack element(s) 9a, 9b can be made of a hard material, having Shore 00 hardness greater than 95 or Shore D from 22 to 35.

In particular, it is underlined that the shoe 1 is completely assembled without stitching, which as is known constitute points of high pressure on the foot of the user and also critical zones with regard to the strength of the upper 3. Also in the inner part or core 3c, it is proposed to eliminate such pressure points.

The heel 8 acts as buttress and confers particular stability to the rear area of the foot during the execution of the athletic action, e.g. pedalling.

According to one aspect of the present invention, the surface 19 of the upper 3 of the shoe 1 comprises a plurality of recesses 20.

As will be clearer hereinbelow, the recesses 20 have the function of decreasing the aerodynamic drag of the upper 3 of the shoe 1 hit by air during the execution of the athletic action or of the pedalling motion in the advancing of the bicycle.

In particular, the recesses 20 determine the formation, on the surface 19 of the upper 3 hit by the air during the execution of the athletic action or pedalling motion, of a turbulent limit layer, which is separated from the surface 19 itself later than what would occur in the case of laminar limit layer.

It follows, therefore, that the motion of the shoe 1 generates a more limited turbulent trail than that which is generated in the case of a laminar limit layer.

This allows decreasing the aerodynamic drag component constituted by the form drag.

In the embodiment represented in the figures, the recesses 20 are particularly distributed in the front area of the upper 3.

More in detail, the recesses 20 are distributed on the movable portion 3b of the upper 3.

In other embodiments of the shoe 1, the recesses 20 could also be distributed on the fixed portion 3a of the upper 3.

In the same embodiment, some of the recesses 20 provided in the movable portion 3b of the upper 3 are constituted by through openings, i.e. by some sort of eyelets or windows.

This characteristic, in addition to lightening the upper 3 overall and making it more flexible, also facilitates the breathing of the foot of the user.

In other embodiments of the invention, all the recesses 20 could be non-through. The recesses 20 for example have oval or substantially polygonal shape; nevertheless they could have any other suitable shape, without limitations.

According to another aspect of the invention, the heel 8 of the shoe 1 comprises at least one channel 21, suitable for channelling the air that hits the upper 3 of the shoe 1 during the execution of the athletic action or of the pedalling motion, in order to further limit the aerodynamic drag of the same.

More in detail, the heel 8 comprises a first and a second channel 21 suitable for channelling the air that hits the upper 3.

The first channel 21 and the second channel 21 are arranged, respectively, on the outer side and on the inner side of the heel 8.

The channels 21 are defined for example by respective bridges 22 shaped by the heel 8 itself and substantially vertically arranged with respect to the support surface of the sole 2 of the shoe 1.

The section of the channels 21 is thus substantially narrow and vertically elongated, still with reference to the support surface of the sole 2.

The section of the channels 21 can vary from one end to the other thereof, in a manner so as to obtain the desired air flow conditions: for example, converging sections can give rise to accelerations of the air during its travel along the channels 21, with advantageous effects in conveying the air towards the zone of the heel 8.

If the rack elements 9a,9b are not slidably mounted in a zone delimited by the closed shell-like body of the fixed portion 3a, the rack elements 9a,9b of the tightening-release means 4,5 can be slidably mounted in the channels 21.

This is a solution that allows optimising the surface area available in the heel 8, and to suitably protect the rack elements 9a,9b.

In other embodiments, the rack elements 9a,9b could be arranged in other zones of the heel 8 surface, in relation to different application needs.

The bridges 22 also have the important function of protecting the control means—in particular the zone of their heads—from possible impact that could damage them or accidentally modify the position set by the user.

The shoe 1 also comprises a heelpiece 30.

The heelpiece 30 is integral with the sole 2 of the shoe.

The heelpiece 30 can for example be made of polymeric material, or of composite material, or of any other suitable material, in relation to the specific needs.

The material with which the heelpiece 30 is made is therefore preferably different from that with which the sole 2 is made; nevertheless, in some embodiments of the invention, the heelpiece 30 and the sole 2 can be made of the same material.

The heelpiece 30 has a shape and a thickness such to be connected with the sole 2 of the shoe.

In other words, the heelpiece 30 does not project with respect to the sole 2 as in other types of shoes, in a manner so as to define, together with the sole 2, a surface lacking discontinuities.

This clearly contributes to limiting the overall aerodynamic drag of the shoe 1.

According to another aspect of the present invention, the heelpiece 30 comprises a respective channel 31, which conveys the air towards a pre-established path, in order to limit the overall aerodynamic drag of the shoe 1.

The channel 31 can for example comprise multiple branches.

It is in any case specified that the channel 31 of the heelpiece 30 could have any other shape suitable for ensuring an effective conveyance of the air towards the rear zone of the heelpiece 30.

With regard to the aerodynamics of the shoe 1, the air hits front of the upper 3, and due to the presence of the recesses 20, a turbulent limit layer is generated on the surface 19 of the upper 3 itself, which ensure that the fluid stream does not move away from the surface 19.

This effect is ensured at least in the front zone of the upper 3, while in the rear zone of the same the stream may easily move away, with consequent increase of the aerodynamic drag.

The presence of the channels 21 in the heel 8, as well as the channels 31 in the heelpiece 30, allows however channelling the fluid stream towards the back of the upper 3, without there being an appreciable moving away of the stream.

This effect is obtained in the entire back region of the upper 3, and in particular also in the area of the heelpiece 30, which only apparently is not hit by the air flow during the execution of the athletic action or of the pedalling motion.

The overall result is therefore a considerable reduction of the form drag of the shoe 1, with respect to the sports shoes or cycling shoes of known type.

The increase of the friction resistance, due to the presence of the recesses 20 in the zone of the front of the upper 3, is amply compensated for by the abovementioned reduction of the form drag thereof, and therefore the overall aerodynamic drag—which as is known is due to the contribution of both—results decisively diminished.

As can be understood, the reduction of the aerodynamic drag of the upper 3 of the shoe 1, in the execution of the athletic action or of the pedalling motion, considerably contributes to limiting the complex turbulent phenomena that are verified in the central movement zone, during the advancing of the man-bicycle system, or in any case in the zone of movement of the shoes 1.

Consequently, the aerodynamic performances are increased, a fact that is particularly important, for example, in professional competitions.

In the sole 2 of the shoe 1, at the front portion, means can be provided for connecting to a device for quick coupling the sole 2 to the pedal of the bicycle, of known type, or to the ski or snowboard.

In one embodiment of the present invention, the heelpiece 30 can be removed from the sole 2 and equipped with fixing means for the connection to the sole 2 itself.

More generally, the fixing means can be of any type suitable for ensuring the safe connection between the heelpiece 30 and the sole 2, preventing accidental separations.

The fixing means allow the user to easily remove the heelpiece 30 from the sole 2.

For example, it is known that the heelpiece 30 is one of the zones of the shoe 1 more subject to wear in walking.

Modifications and variants of the invention are possible within the protective scope defined by the claims.

The invention claimed is:

1. A sports shoe for running or for cycling, comprising:
a sole and an upper that rises up from said sole, wherein said upper comprises mutually displaceable portions and an inner part, and tightening-release means adjustably connecting the mutually displaceable portions, wherein said mutually displaceable portions define a groove therebetween, said groove comprising a first section intersecting with a second section, wherein the first section has a substantially oblique progression and the second section is substantially horizontal to the sole;
wherein said inner part defines an inner housing volume (RZ) for encompassing a foot of a user,
wherein said inner part comprises an upper portion,
wherein said inner part comprises a ground resting portion for coming into contact directly with the ground when said inner part is extracted from the shoe, or with said inner surface of said sole, when said inner part is inserted into the upper, wherein said upper portion rises up from said ground resting portion, and wherein said inner part has a thickness,
wherein said upper portion is made of at least one of an elasticated material and a woven material.

2. The sports shoe according to claim 1, wherein said inner part is removable from said sports shoe.

3. The sports shoe according to claim 1, wherein said upper portion comprises a hole for the insertion of the user's foot and wherein said upper portion comprises an annular or tubular component.

4. The sports shoe according to claim 1, wherein said upper portion is made in a single piece.

5. The sports shoe according to claim 1, wherein said inner part is made from at least one of an elasticated fabric and a woven material, wherein said elasticated fabric and/or woven material is at least at least one of breathable and impermeable.

6. The sports shoe according to claim 1, wherein said inner part is made from at least one of an elasticated fabric and a woven material woven in a circular manner, or comprising a woven tube.

7. The sports shoe according to claim 1, wherein said inner part is made from at least one of an elasticated fabric and a woven material, wherein said at least one of an elasticated fabric and woven material is a fabric with high breathability laminated with a layer of foam, or a synthetic rubber based on polychloroprene.

8. The sports shoe according to claim 1, wherein said inner part is made from at least one of an elasticated fabric and a woven material, wherein said woven material comprises a three-dimensional mesh comprising at least one thread of thermosetting polyester.

9. The sports shoe according to claim 1, wherein said inner part is made from at least one of an elasticated fabric and a woven material comprising a composite yarn material comprising fibres, or carbon fibres, able to assume the desired shape of said inner part.

10. The sports shoe according to claim 1, wherein said inner part is made from at least one of an elasticated fabric and comprising a yarn comprising at least one detecting system for detecting the at least one of physiological or vital parameters of the body of the user, including comfort and positioning of the foot of the user and the power exerted by the foot.

11. The sports shoe according to claim 1, wherein said inner part has a constant thickness throughout, with respect to said sports shoe.

12. The sports shoe according to claim 1, wherein said inner part has a greater thickness in at least one of the ground resting portion or at the back of the user's foot.

13. The sports shoe according to claim 1, wherein said ground resting portion of said inner part comprises at least one of a polymeric material, rubber, silicon, polyurethane, thermoplastic rubber, and vulcanized rubber.

14. The sports shoe according to claim 1, wherein said ground resting portion is applied to said inner part through at least one of moulding, gluing, impregnation, stitching and welding.

15. The sports shoe according to claim 1, wherein said ground resting portion has a surface pattern for resting on the ground of the tread type or equipped with non-slip grooves.

16. The sports shoe according to claim 1, wherein said ground resting portion partially rises on the lateral edges thereof.

17. The sports shoe according claim 1, wherein said inner part has a hole for the insertion of the user's foot and a tongue arranged at said hole in the rear part of the heel.

18. The sports shoe of claim 8, wherein said at least one of an elasticated fabric and woven material is coupled with a fabric comprising at least one of a synthetic polyurethane fibre, hook and loop fasteners, elastam, microfiber, or a synthetic fabric with high impermeability and breathability capabilities.

19. The sports shoe of claim 18, wherein said synthetic fabric comprises microporous polytetrafluoroethylene.

20. The sports shoe of claim 8, wherein said at least one of an elasticated fabric and woven material is a mesh equipped with through openings or partial through openings.

21. The sports shoe according to claim 1, wherein said ground resting portion of said inner part comprises a material having a hardness Shore 00 comprised between 70 and 80.

22. The sports shoe according to claim 1, wherein a rear portion of a heel area of the ground resting portion has a thickness of about 5 mm.

23. The sports shoe according to claim 1, wherein the inner part comprises at least one of an elasticated fabric and a woven material having varying densities.

24. The sports shoe of claim 1, wherein the mutually displaceable portions comprise a fixed portion and a movable portion, said movable portion at least partially displaceable with respect to the fixed portion.

25. The sports shoe of claim 1, wherein the tightening-release means comprise two separate cable elements, each cable element comprising a first end affixed to the movable portion and a second end adjustably affixed with the fixed portion.

26. The sports shoe of claim 25, wherein the at least one cable element engages the movable portion at a plurality of zones.

27. A sports shoe for running or for cycling, comprising:
a sole and an upper that rises up from said sole, wherein said upper comprises mutually displaceable portions and an inner part, and tightening-release means adjustably connecting the mutually displaceable portions, wherein said mutually displaceable portions define a groove therebetween, said groove comprising a first section intersecting with a second section, wherein the first section has a substantially oblique progression and the second section is substantially horizontal to the sole;
wherein said inner part defines an inner housing volume (RZ) for encompassing a foot of a user,
wherein said inner part comprises an upper portion,
wherein said inner part comprises a ground resting portion for coming into contact directly with the ground when said inner part is extracted from the shoe for running, or with said inner surface of said sole, when said inner part is inserted into the upper for cycling,
wherein said upper portion rises up from said ground resting portion, and wherein said inner part has a thickness,
wherein said upper portion is made of an elasticated material and/or a woven material.

* * * * *